United States Patent
Hasegawa et al.

(10) Patent No.: US 10,138,123 B2
(45) Date of Patent: Nov. 27, 2018

(54) METHOD FOR REGENERATING WORKING SOLUTION USED FOR PRODUCTION OF HYDROGEN PEROXIDE AND METHOD FOR PRODUCING HYDROGEN PEROXIDE USING REGENERATED WORKING SOLUTION

(71) Applicant: MITSUBISHI GAS CHEMICAL COMPANY, INC., Chiyoda-ku (JP)

(72) Inventors: Hiroshi Hasegawa, Ibaraki (JP); Yukako Kozawa, Ibaraki (JP); Motoharu Takeuchi, Ibaraki (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 347 days.

(21) Appl. No.: 14/913,597

(22) PCT Filed: Aug. 8, 2014

(86) PCT No.: PCT/JP2014/070973
§ 371 (c)(1),
(2) Date: Feb. 22, 2016

(87) PCT Pub. No.: WO2015/025735
PCT Pub. Date: Feb. 26, 2015

(65) Prior Publication Data
US 2016/0200574 A1    Jul. 14, 2016

(30) Foreign Application Priority Data

Aug. 23, 2013  (JP) ................................. 2013-173292

(51) Int. Cl.
| | |
|---|---|
| C01B 15/023 | (2006.01) |
| C07C 29/143 | (2006.01) |
| B01J 23/86 | (2006.01) |
| B01J 29/00 | (2006.01) |

(52) U.S. Cl.
CPC .......... C01B 15/023 (2013.01); B01J 23/868 (2013.01); B01J 29/00 (2013.01); C07C 29/143 (2013.01); *Y02P 20/584* (2015.11); *Y02P 20/588* (2015.11)

(58) Field of Classification Search
None
See application file for complete search history.

(56) References Cited

U.S. PATENT DOCUMENTS

| | | |
|---|---|---|
| 2009/0018013 A1 | 1/2009 | Hasegawa et al. |
| 2009/0169469 A1 | 7/2009 | Sakaitani et al. |

FOREIGN PATENT DOCUMENTS

| | | |
|---|---|---|
| JP | 6-135705 A | 5/1994 |
| JP | 2008-87992 A | 4/2008 |
| JP | 2008-120631 A | 5/2008 |
| JP | 2009-34663 A | 2/2009 |
| WO | WO 2007/129769 A1 | 11/2007 |

OTHER PUBLICATIONS

International Search Report dated Nov. 18, 2014 in PCT/JP2014/070973 (with English language translation).

*Primary Examiner* — Melissa S Swain
(74) *Attorney, Agent, or Firm* — Oblon, McClelland, Maier & Neustadt, L.L.P.

(57) ABSTRACT

In the production of hydrogen peroxide, when ketone forms are increased upon conversion from higher alcohol components in organic solvents, such increased levels of ketone forms reduce the water content in a working solution and lead to deterioration of catalytic activity. Moreover, increased levels of ketone forms reduce the solubility of anthrahydroquinone compounds and may cause an obstacle to stable and safe operation in the production of hydrogen peroxide due to crystallization and deposition of the anthrahydroquinone compounds.

The object of the present invention is to provide a process in which polar solvent-derived altered substances (ketone forms) in a working solution provided for use in the production of hydrogen peroxide via the anthraquinone process are regenerated into the original alcohol components to thereby improve the production efficiency of hydrogen peroxide.

From a working solution which has been used for many years, organic solvent components containing ketone forms are separated by distillation and hydrogenated in the presence of a metal catalyst to regenerate the organic solvent components into the original alcohol components, whereby hydrogen peroxide can be produced more efficiently.

10 Claims, No Drawings

METHOD FOR REGENERATING WORKING SOLUTION USED FOR PRODUCTION OF HYDROGEN PEROXIDE AND METHOD FOR PRODUCING HYDROGEN PEROXIDE USING REGENERATED WORKING SOLUTION

TECHNICAL FIELD

The present invention relates to a process for regeneration of a working solution provided for use in the production of hydrogen peroxide via the anthraquinone process. More specifically, the present invention relates to a process for regeneration of a working solution, which involves hydrogenation treatment in the presence of a metal catalyst to thereby regenerate polar solvent-derived altered substances in the working solution into the original polar solvent components, as well as a process for production of hydrogen peroxide using the working solution thus treated.

BACKGROUND ART

A major process which is now industrially used for production of hydrogen peroxide is a process using an anthraquinone compound as a reaction medium, which is generally referred to as the anthraquinone process. An anthraquinone compound is used by being dissolved in an appropriate organic solvent. For this purpose, organic solvents may be used either alone or as a mixture, and it is common to use a mixture of two types of solvents, i.e., a polar solvent and a nonpolar solvent. A solution prepared by dissolving an anthraquinone compound(s) in an organic solvent(s) is referred to as a working solution.

The anthraquinone process involves a reduction step where an anthraquinone compound(s) in the above working solution is hydrogenated in the presence of a catalyst to generate an anthrahydroquinone compound(s), followed by an oxidation step where the anthrahydroquinone compound(s) is oxidized with air or with an oxygen-containing gas and thereby converted back into the anthraquinone compound(s) simultaneously with the generation of hydrogen peroxide. Hydrogen peroxide generated in the working solution is usually extracted with water and separated from the working solution. The working solution from which hydrogen peroxide has been extracted is returned again to the reduction step, thereby forming a cycle process. This process allows production of hydrogen peroxide substantially from hydrogen and air, and is therefore a very efficient and effective process. Using this cycle process, hydrogen peroxide has already been produced on an industrial scale.

During repeated cycles of hydrogenation and oxidation, organic solvents in the working solution will also be altered and accumulated as by-products. These by-products are mainly composed of ketone forms generated upon dehydrogenation of higher alcohols which are polar solvents in the working solution. A working solution enriched with ketone forms reduces the desired content of water which can be incorporated thereinto. As a result, such by-products lead to deterioration of catalytic activity and may cause an obstacle to safe and stable operation. Moreover, these by-products also include oxidized and decomposed products of organic solvent components. More specifically, carboxylic acids, polyols, phenols and so on are detected. These by-products will alter the various physical and chemical properties of the working solution, including specific gravity, viscosity, surface tension, etc., and therefore will cause a reduction in the production efficiency of hydrogen peroxide through the steps of reduction, oxidation and extraction of the working solution.

Until now, some processes have been proposed to remove various by-products from a working solution which has been used for many years and to regenerate such a working solution. A known example is a process in which the reduced anthraquinone compounds are contacted with an aqueous alkaline solution to thereby remove by-products of the anthraquinone compounds, which do not contribute to the generation of hydrogen peroxide.

Likewise, a known example based on chemical treatment is a process in which a halide of aluminum, ammonium or the like is used in solid or aqueous solution form to treat a working solution at 100° C. to 170° C. and thereby regenerate by-products of anthraquinone compounds.

In addition, another known example is a process in which a working solution is treated with ozone and then extracted with an aqueous solution of an alkali metal hydroxide, and the working solution thus extracted and separated is contacted with activated alumina or activated magnesia.

On the other hand, a process is also known which comprises conducting the first stage of distillation to separate organic solvents from a working solution and then conducting the second stage of distillation to separate anthraquinone compounds and monoanthracene-based low-boiling substances, during which blockage caused by crystallization of distillates is prevented.

In addition, Patent Document 1 discloses a process for production of hydrogen peroxide, characterized by having a first distillation step of recovering organic solvents from a working solution by distillation performed at an atmospheric pressure or a lower pressure and a second distillation step of, following the first distillation step, recovering anthraquinone compounds by distillation performed at a still lower pressure at a temperature of 200° C. or higher for a residence time of 1 hour or longer, and characterized by treating the working solution prepared from all the distillates with a regeneration catalyst.

Patent Document 2 discloses a process in which organic solvent-derived low-boiling denatured substances are removed by azeotropic distillation with an aqueous alkaline solution.

In addition, Patent Document 3 discloses a process in which a working solution is distilled and the resulting organic solvents are treated by being contacted with water to remove organic solvent-derived denatured substances.

PRIOR ART DOCUMENTS

Patent Documents

Patent Document 1: WO2007/129769
Patent Document 2: JP Patent Publication No. 2008-87992 A
Patent Document 3: JP Patent Publication No. 2008-120631 A

SUMMARY OF THE INVENTION

Problem to be Solved by the Invention

As described above, in the proposed techniques, there are reports of a process for extraction and/or removal of by-products from the reaction medium and a process for removal of solvent-derived altered substances. However, there is no proposal on techniques to regenerate and/or remove the ketone forms of higher alcohol components, which are polar solvents among organic solvents. Increased levels of ketone forms in a working solution reduce the water content in the working solution and lead to deterioration of catalytic activity, and further may cause an obstacle to safe operation.

The object of the present invention is to provide a process in which polar solvent-derived ketone forms in a working solution which has been used for many years in the production of hydrogen peroxide via the anthraquinone process are regenerated into the original alcohol components to thereby improve the production efficiency of hydrogen peroxide.

Means to Solve the Problem

The inventors of the present invention have found that a working solution provided for use is distilled to separate organic solvent components containing ketone forms, which are then hydrogenated in the presence of a metal catalyst and thereby regenerated into the original alcohol components, whereby hydrogen peroxide can be produced efficiently. This finding led to the completion of the present invention.

Namely, the present invention is as follows.
1. A process for regeneration of a working solution provided for continuous use in the production of hydrogen peroxide via the anthraquinone process, which comprises the step of distilling the working solution to separate organic solvent components containing an alcohol and the ketone form of the alcohol, and the step of subjecting the resulting organic solvent components to hydrogenation treatment in the presence of a metal catalyst to regenerate the ketone form back into the original alcohol.
2. The process for regeneration of a working solution according to 1 above, wherein as a result of hydrogenation treatment of the organic solvent components in the presence of a metal catalyst, the remaining percentage of the ketone form in the organic solvent components (=ketone form/organic solvent components×100) is adjusted to 10% by mass or less. 3. The process for regeneration of a working solution according to 1 above, wherein the metal catalyst is a metal compound comprising one or more members selected from palladium, rhodium, ruthenium, platinum, copper or chromium.
4. The process for regeneration of a working solution according to 1 above, wherein the metal catalyst is a metal compound comprising copper and/or chromium.
5. The process for regeneration of a working solution according to 1 above, wherein the amount of the metal catalyst added is 0.05% by mass to 10% by mass relative to the mass of the organic solvent components.
6. The process for regeneration of a working solution according to 1 above, wherein the pressure for the hydrogenation treatment is atmospheric pressure to 10 MPa.
7. The process for regeneration of a working solution according to 1 above, wherein the hydrogenation temperature for the hydrogenation treatment is 140° C. to 230° C.
8. The process for regeneration of a working solution according to 1 above, wherein the time for the hydrogenation treatment is 0.5 hours to 100 hours.
9. The process for regeneration of a working solution according to 1 above, which comprises the step of treating the organic solvent components after the hydrogenation treatment by contacting the same with water and/or an aqueous alkaline solution.
10. A process for production of hydrogen peroxide via the anthraquinone process, which uses the working solution regenerated by the process according to any one of 1 to 9 above.
11. Hydrogen peroxide produced by the process for production according to 10 above.

Effects of the Invention

The present invention enables the regeneration and reuse of polar solvent-derived altered substances in a working solution, so that a reduction can be expected in the amount of solvent(s) to be used and, as a consequence, a reduction can be achieved in the production cost. Furthermore, a reduction can be expected in the risk of catalyst deactivation, and hence an efficient process can be achieved.

DESCRIPTION OF EMBODIMENTS

The present invention will be described in more detail below. The following embodiments are illustrated to describe the present invention, and it is not intended to limit the present invention only to these embodiments. The present invention can be implemented in various modes, without departing from the spirit of the present invention.

As described above, a solution prepared by dissolving an anthraquinone compound(s) in an organic solvent(s) is referred to as a working solution. Preferred anthraquinone compounds to be used in the present invention are alkylanthraquinones, alkyltetrahydroanthraquinones or mixtures thereof. Alkylanthraquinones or alkyltetrahydroanthraquinones used for this purpose may be in the form of a mixture composed of several types of alkylanthraquinones or alkyltetrahydroanthraquinones. Alkylanthraquinones may be exemplified by ethylanthraquinone, t-butylanthraquinone, amylanthraquinone, etc. Likewise, alkyltetrahydroanthraquinones may be exemplified by ethyltetrahydroanthraquinone, t-butyltetrahydroanthraquinone, amyltetrahydroanthraquinone, etc.

As an organic solvent, it is possible to use either a nonpolar solvent or a polar solvent, but preferred is a solvent containing both of them. Examples of a nonpolar solvent include aromatic hydrocarbons, as exemplified by benzene or benzene derivatives having an alkyl substituent(s) containing 1 to 5 carbon atoms. Examples of a polar solvent include higher alcohols, carboxylic acid esters, tetra-substituted ureas, cyclic ureas, trioctyl phosphate, etc.

In the present invention, the organic solvents recovered by distillation from the working solution which has been used for many years are hydrogenated in the presence of a hydrogenation catalyst (i.e., a metal catalyst). Such a metal catalyst is supported on a carrier and comprises a metal compound preferably containing at least one or more members selected from copper, chromium, palladium, rhodium, ruthenium or platinum. Particularly preferred is a catalyst containing copper and/or chromium.

Moreover, such a catalyst compound is generally in a metal state, but may also be in the form of an oxide which is readily reduced to the metal state under reaction conditions. Moreover, these metals may be in the form of being supported on a carrier. The catalyst amount is not critical to the effect of the present invention and may be an amount required for the hydrogenation reaction to proceed well.

The process for production of hydrogen peroxide according to the present invention comprises a step where a working solution which has been used for a long period of time and whose organic solvent components have been oxidized and deteriorated as a result of continuous and repeated use is separated by distillation operation into a reaction medium containing alkylanthraquinones and/or alkyltetrahydroanthraquinones and organic solvent components containing ketone forms, and these organic solvent components are further subjected to hydrogenation treatment in the presence of a metal catalyst to thereby regenerate the ketone forms in the organic solvent components into the original alcohol components, which are then mixed with the alkylanthraquinones and/or alkyltetrahydroanthraquinones separated as described above and provided for reuse in the production of hydrogen peroxide.

It should be noted that organic solvent components recovered at various points during the process of hydrogen peroxide production (e.g., organic solvents recovered from the exhaust gas in the oxidation step) may also be mixed with the above working solution or organic solvent components and subjected to distillation and hydrogenation treatment.

The working solution to be used in the present invention is enriched with the oxidized and deteriorated forms of the organic solvent components as a result of continuous and repeated use. However, it is feared that abnormal decomposition will be caused when hydrogen peroxide remains in the working solution during the distillation operation required for separation into the reaction medium and the organic solvent components. For this reason, it is preferred that the above working solution is in a state being free from hydrogen peroxide by being fully contacted with water prior to the distillation operation. Water used for this purpose is preferably distilled water, ion exchanged water, or purified water obtained by reverse osmosis, etc. Water purified by any other techniques may also be used preferably for this purpose. In particular, pure water is preferred as water used for washing purposes.

As a means for mixing the above working solution with water, any generally known technique may be used. Examples include, but are not limited to, stirring, shaking, and bubbling with an inert gas, as well as parallel-flow and cross-flow contact techniques, although any technique may be used as long as it allows efficient contact between the above working solution and water.

There is no critical upper limit for the volume of water to be contacted, and it may be selected as appropriate for the type of unit to be used for contact and/or for the convenience of the operation. Likewise, there is no critical upper limit for the time required for contact between the working solution and water, and it may be selected as appropriate for the type of unit to be used for contact and/or for the convenience of the operation. In addition, the temperature required for contact between the working solution and water is in the range of 0° C. to 70° C., preferably 10° C. to 60° C., and particularly preferably 20° C. to 50° C. Within this range, hydrogen peroxide can be removed efficiently. Moreover, the pressure during contact between the working solution and water is not limited in any way, but it is generally favorable that the pressure is maintained at normal pressure. After being contacted, the water is separated and eliminated from the working solution.

The working solution which has been used for a long period of time is separated by distillation operation into a reaction medium containing alkylanthraquinones and/or alkyltetrahydroanthraquinones and organic solvent components. During the distillation operation intended in the present invention, the organic solvent components in the working solution are preferably distilled at normal pressure or a lower pressure, although any commonly used distillation equipment may be used for this purpose without any particular limitation. Examples include a batch distillation unit, a continuous distillation unit, a thin-film distillation unit and so on. As to detailed operation conditions, those disclosed in WO2007/129769 may be applied. Among the distillation conditions, the temperature and the pressure cannot be defined uniformly because they are selected as appropriate for the type of solvent(s) used in the working solution. However, they are selected from among the conditions as shown below. The pressure is suitably 1 kPa to 100 kPa (atmospheric pressure), more preferably 5 to 80 kPa, and even more preferably 5 to 30 kPa. The temperature is determined as conditions where distillation is continued until the residual amount of solvents is 5% by mass or less. In general, when the temperature reaches about 50° C. to 100° C. higher than the pot temperature at which the solvents start to be distilled, such a point is assumed to be the completion of distillation. For example, if the solvents start to be distilled at a pot temperature of 130° C. under a reduced pressure of 13 kPa, distillation may be stopped at a point where the pot temperature reaches 200° C.

<Regeneration of Working Solution>

The above organic solvent components recovered by distillation in the present invention are hydrogenated in the presence of a metal catalyst to thereby regenerate the oxidized and deteriorated forms of the organic solvent components into the original organic solvent components. For this purpose, any commonly used pressurizable reaction equipment may be used without any particular limitation. Examples include a batch reactor, a continuous reactor and so on, with a batch reactor being preferred. However, it is more advantageous for hydrogenation reaction to ensure that the organic solvent components, the hydrogenation catalyst and hydrogen are mixed well. As a mixing means, any generally known technique may be used. Examples include, but are not limited to, stirring, shaking, and circulation of the reaction mixture, although any technique may be used as long as it allows efficient contact of the above organic solvent components, the hydrogenation catalyst and hydrogen.

<Hydrogenation of Organic Solvents Recovered by Distillation>

In the present invention, the organic solvents recovered by distillation are subjected to hydrogenation reaction. The amount of the hydrogenation catalyst to be added is not limited in any way as long as it is an amount sufficient for the hydrogenation reaction to proceed. However, the amount of the hydrogenation catalyst calculated as a metal component is preferably 0.05% to 10% by mass, more preferably 0.1% to 8% by mass, and particularly preferably 0.2% to 5% by mass, relative to the weight of the organic solvent components.

Likewise, the hydrogenation temperature and the hydrogenation pressure are also not limited in any way, although the hydrogenation temperature is preferably 100° C. to 230° C., more preferably 140° C. to 230° C., and a particularly preferred temperature is 150° C. to 210° C.

The hydrogenation pressure is atmospheric pressure or higher, preferably 0.8 MPa or higher, more preferably 1.2 MPa or higher, and particularly preferably 1.8 MPa or higher. The maximum pressure depends on the type of hydrogenation unit, but it is preferably 10 MPa or lower in terms of safety.

The hydrogenation time is also not limited in any way and may be set to any period of time not exceeding the completion of the hydrogenation reaction, but it is preferably 0.5 hours to 100 hours, more preferably 1 hour to 80 hours, and particularly preferably 2 hours to 50 hours. As to the end point of the hydrogenation reaction, for example, a point where the remaining percentage of ketone forms in the organic solvents is 10% or less is assumed to be the completion of the reaction, although a lower value is preferred and may be selected as appropriate. It is more preferably 8% or less, and even more preferably 7% or less.

In the present invention, the hydrogenated organic solvents are taken out from the reactor and separated from the hydrogenation catalyst. As a separation means, any generally known means may be used. Examples include, but are not limited to, a filter paper, a sintered metal filter, a metal fiber filter, a resin filter, and centrifugation, although any means (including the shape of a member for separation) may be used as long as it allows efficient separation between the above organic solvent components and the hydrogenation catalyst.

In the present invention, the hydrogenated organic solvent components separated as described above are preferably subjected to azeotropic distillation with an aqueous alkaline solution or subjected to contact treatment with an aqueous alkaline solution or water. This allows removal of the altered substances other than ketone forms, i.e., the oxidized and deteriorated substances which cannot be easily removed by distillation or hydrogenation reaction, as exemplified by dimethylbenzoic acid, alkylphthalic acid anhydrides, aliphatic carboxylic acids, trimethylphenol and 2,6-dimethyl-4-heptanediol. As to detailed operation conditions, those disclosed in JP Patent Publication No. 2008-87992 or JP Patent Publication No. 2008-120631 may be applied.

In the present invention, the organic solvent components obtained by the above operation are mixed with the reaction medium recovered by the above distillation operation or with a fresh reaction medium, and then returned for reuse as a working solution in the process of hydrogen peroxide production.

EXAMPLES

The present invention will be further described in more detail by way of the following illustrative examples, although the present invention is not limited to these examples. In the present invention, it should be noted that pseudocumene (PSC) was used as an aromatic hydrocarbon serving as a nonpolar solvent in the working solution, while diisobutylcarbinol (DIBC) was used as a higher alcohol serving as a polar solvent in the working solution. The ketone form derived from diisobutylcarbinol is diisobutyl ketone (DIBK), and individual organic solvent components were measured by gas chromatography (GC). Among organic solvent components, the altered substances of the organic solvents, which are impossible to regenerate by hydrogenation treatment, were confirmed as other components, as exemplified by dimethylbenzoic acid, alkylphthalic acid anhydrides, aliphatic carboxylic acids, trimethylphenol and 2,6-dimethyl-4-heptanediol.

<Measurement of Acid Value in Solvent>

The acid value of a solvent was measured according to JIS-K0070. Detailed procedures are as follows. First, to a flask, 40 mL of a solvent sample and 20 mL of an aqueous sodium carbonate solution (N/10) were each added and weighed, followed by extraction at 50° C. for 15 minutes. The extracted contents were allowed to stand in a separatory funnel, and the generated sodium carbonate solution layer (lower layer) was washed with 20 ml of pseudocumene, followed by addition of pure water to 5 mL of the sodium carbonate solution layer to give a sample of 40 ml, which was then titrated with N/20 hydrochloric acid. The acid value A of the solvent sample was then determined on the basis of the following equation:

$$A=(B/R-C/S) \times N \times F \times U/V \times 1000$$

(in which A: acid value (measured value of acid component (mmol/L)), B: blank titer (mL), C: sample titer (mL), R: blank volume (5 mL), S: sample volume titrated (5 mL), N: titrant concentration (0.05 mol/L), F: titrant factor, U: extract volume (mL) during extraction, and V: sample volume (mL) during extraction).

<Measurement of Water Content in Working Solution>

For measurement of the water content in the prepared working solution, Karl Fischer MKS-520 (Kyoto Electronics Manufacturing Co. Ltd., Japan) was used. Detailed procedures are as follows. First, the prepared working solution was taken into a 2 ml whole pipette and injected into a titration cell in the Karl Fischer MKS-520 (Kyoto Electronics Manufacturing Co. Ltd., Japan). The sample was titrated by using AQUAMICRON Titrant SS 3 mg as a titrant to determine the water content by volume titration.

<Test for Activity of Working Solution>

The working solution obtained by the above treatment was tested to confirm its performance in the following manner by using a batch evaluation unit equipped with a stirring blade. The above batch reaction vessel was charged with 1 part by weight of a catalyst and 20 parts by weight of the working solution. After the reaction vessel was sealed, the reaction system was purged with hydrogen. The stirring blade was rotated at 1000 rpm for 30 minutes, and the amount of hydrogen absorption per unit catalyst was measured. The reaction temperature was set to 30° C. and the reaction pressure was controlled to normal pressure. The catalyst used here was the silica-supported palladium catalyst disclosed in JP 9-271670 A.

Reference Example 1

<Recovery of Organic Solvent Components which are Source Materials to be Treated>

A working solution which had actually been used for many years in a hydrogen peroxide production unit was used as a working solution provided for use in the first distillation step in the present invention. The working solution (2000 ml) was taken out from the hydrogen peroxide production unit. The reaction medium in the working solution is composed of amylanthraquinone and amyltetrahydroanthraquinone. For recovery of organic solvent components during the first stage, a 1000 ml flask equipped with a distillation unit was charged in advance with 400 ml of the working solution, the degree of vacuum was controlled to 13 kPa and the temperature was elevated from room temperature. Once distillation has started at the time point where the pot temperature reached 130° C., the liquid volume in the flask will be reduced. For this reason, the remainder of the working solution was added successively and the addition was stopped at the time point where the total amount charged was 2000 ml. After stopping the addition of the working solution, distillation was continued until the distillation pot temperature reached 200° C., which required 2 hours, to thereby recover the organic solvent components. The anthraquinone compounds remaining at this time in the flask in the distillation pot are referred to as "the separated reaction medium." As a result of analysis by GC, the organic solvent components in this separated reaction medium were found to be 1% by mass or less in total.

On the other hand, the recovered organic solvent components were 1400 ml and are referred to as the distillation-recovered solvent. As a result of analysis by GC, the organic solvent components in this distillation-recovered solvent were found to be pseudocumene/diisobutylcarbinol/diisobutyl ketone=62.4% by mass/11.8% by mass/25.4% by mass. Moreover, this distillation-recovered solvent was found to have an acid value of 84 mg-KOH/g (Table 1).

<Preparation of Working Solution>

The above "separated reaction medium" (the residue in the pot upon recovery by distillation) and the distillation-recovered solvent were mixed together such that the concentration of solid contents (amylanthraquinone and amyltetrahydroanthraquinone) was 250 g/L. After pure water (5 g) was further added, the mixture was stirred and then allowed to stand at room temperature (20° C. to 25° C.) for about 2 hours to thereby obtain a working solution. The resulting working solution was found to have a water content of 2.4 g/L (Table 1).

In light of the fact that a working solution preferably contains an appropriate amount of water, it should be noted that 5 g of pure water (which is greater than the saturated water content) was added in advance to the above mixture prior to measurement of the water content (saturated water content) actually contained in the mixture. The same measurement was also conducted in each of the examples and reference examples shown below, and the results of water content evaluation in these examples and others will be described later.

<Test for Activity of Working Solution>

The working solution prepared above was tested for its activity. The amount of hydrogen absorption obtained here was used as a criterion and defined to be 100% relative hydrogen absorption (Table 1).

Example 1

<Hydrogenation of Distillation-Recovered Solvent>

An autoclave was charged with the above distillation-recovered solvent (900 g) and N203SD (Cu—Cr catalyst; JGC Catalysts and Chemicals Ltd., Japan) as a catalyst in an amount of 9 g (1% by mass relative to the distillation-recovered solvent), followed by hydrogenation reaction for 7 hours. The reaction temperature was set to 200° C. and the reaction pressure was controlled to 2.0 MPa. After completion of the hydrogenation reaction, the reaction mixture was allowed to stand until reaching room temperature, and the catalyst was then removed by filtration through an ADVANTEC filter No. 1. The distillation-recovered solvent receiving the hydrogenation reaction is referred to as the hydrogenated solvent. As a result of analysis by GC, the components of this hydrogenated solvent were found to be pseudocumene/diisobutylcarbinol/diisobutyl ketone=62.4% by mass/30.8% by mass/6.4% by mass. The results of GC analysis on the hydrogenated solvent components over the time course of the hydrogenation reaction are shown in Table 1. Moreover, this hydrogenated solvent was found to have an acid value of 81 mg-KOH/g (Table 1).

<Preparation of Working Solution>

The above "separated reaction medium" (the residue in the pot upon recovery by distillation) and the hydrogenated solvent were mixed together such that the concentration of solid contents (amylanthraquinone and amyltetrahydroanthraquinone) was 250 g/L. After pure water (5 g) was further added, the mixture was stirred and then allowed to stand at room temperature (20° C. to 25° C.) for about 2 hours to thereby obtain a working solution. The resulting working solution was found to have a water content of 3.6 g/L (Table 1).

<Test for Activity of Working Solution>

The resulting working solution was tested for its activity. The relative hydrogen absorption rate of this working solution was found to be 153% (Table 1).

Example 2

<Hydrogenation of Distillation-Recovered Solvent>

The distillation-recovered solvent was subjected to hydrogenation treatment for 80 hours in total under the same conditions as used in Example 1, except that the catalyst amount was set to 0.4% by mass relative to the distillation-recovered solvent, the reaction temperature was set to 160° C. and the reaction pressure was controlled to 1.6 MPa. The hydrogenated solvent components were found to be pseudocumene/diisobutylcarbinol/diisobutyl ketone=62.2% by mass/30.3% by mass/6.9% by mass. The results of GC analysis on the hydrogenated solvent components over the time course of the hydrogenation reaction are shown in Table 1. Moreover, this hydrogenated solvent was found to have an acid value of 82 mg-KOH/g (Table 1).

<Preparation of Working Solution>

The same procedure as shown in Example 1 was repeated to prepare a working solution. This working solution was found to have a water content of 3.5 g/L (Table 1).

<Test for Activity of Working Solution>

The same procedure as shown in Example 1 was repeated to test the resulting working solution for its activity. The relative hydrogen absorption rate of this working solution was found to be 151% (Table 1).

Example 3

<Hydrogenation of Distillation-Recovered Solvent>

The distillation-recovered solvent was subjected to hydrogenation treatment for 9 hours under the same conditions as used in Example 1, except that the reaction temperature was set to 160° C. and the reaction pressure was controlled to 2.0 MPa. The hydrogenated solvent components were found to be pseudocumene/diisobutylcarbinol/diisobutyl ketone=62.3% by mass/31.1% by mass/6.1% by mass. The results of GC analysis on the hydrogenated solvent components over the time course of the hydrogenation reaction are shown in Table 1. Moreover, this hydrogenated solvent was found to have an acid value of 82 mg-KOH/g (Table 1).

<Preparation of Working Solution>

The same procedure as shown in Example 1 was repeated to prepare a working solution. This working solution was found to have a water content of 3.6 g/L (Table 1).

<Test for Activity of Working Solution>

The same procedure as shown in Example 1 was repeated to test the resulting working solution for its activity. The relative hydrogen absorption rate of this working solution was found to be 152% (Table 1).

Example 4

<Hydrogenation of Distillation-Recovered Solvent>

The distillation-recovered solvent was subjected to hydrogenation treatment for 8.5 hours in total in the same manner as shown in Example 1, except that an autoclave was charged with the distillation-recovered solvent in an amount of 1800 g, which is twice that used in Example 1, and the catalyst in an amount of 14.4 g, and the reaction temperature was controlled to start from 160° C. and then elevated to 200° C. after 2 hours from the initiation of the reaction. The hydrogenated solvent components were found to be pseudocumene/diisobutylcarbinol/diisobutyl ketone=62.3% by mass/30.6% by mass/6.6% by mass. The results of GC analysis on the hydrogenated solvent components over the time course of the hydrogenation reaction are shown in Table 1. Moreover, this hydrogenated solvent was found to have an acid value of 81 mg-KOH/g (Table 1).

<Preparation of Working Solution>

The same procedure as shown in Example 1 was repeated to prepare a working solution. This working solution was found to have a water content of 3.5 g/L (Table 1).

<Test for Activity of Working Solution>

The same procedure as shown in Example 1 was repeated to test the resulting working solution for its activity. The relative hydrogen absorption rate of this working solution was found to be 151% (Table 1).

Example 5

<Hydrogenation of Distillation-Recovered Solvent>

The same procedure as shown in Example 1 was repeated to effect hydrogenation for 12.5 hours, except that the reaction temperature was set to 220° C. and the reaction pressure was controlled to 1.0 MPa. The hydrogenated solvent components were found to be pseudocumene/diisobutylcarbinol/diisobutyl ketone=62.4% by mass/30.8% by mass/6.4% by mass. The results of GC analysis on the hydrogenated solvent components over the time course of the hydrogenation reaction are shown in Table 1. Moreover, this hydrogenated solvent was found to have an acid value of 82 mg-KOH/g (Table 1).

<Preparation of Working Solution>

The same procedure as shown in Example 1 was repeated to prepare a working solution. This working solution was found to have a water content of 3.6 g/L (Table 1).

<Test for Activity of Working Solution>

The same procedure as shown in Example 1 was repeated to test the resulting working solution for its activity. The relative hydrogen absorption rate of this working solution was found to be 152% (Table 1).

Reference Example 2

<Preparation of Working Solution>

First, a mixed solution was prepared to consist of 60% by volume of fresh pseudocumene and 40% by volume of diisobutylcarbinol. The components of this mixed solvent were found to be pseudocumene/diisobutylcarbinol/diisobutyl ketone=60.8% by mass/38.1% by mass/1.0% by mass. Moreover, this mixed solvent was found to have an acid value of 0 mg-KOH/g (Table 1).

To this mixed solvent, fresh amylanthraquinone (83 g) was dissolved to give an amylanthraquinone concentration of 0.6 mol/L. After pure water (5 g) was further added, the mixture was stirred and then allowed to stand at room temperature (20° C. to 25° C.) for about 2 hours to thereby obtain a working solution. The resulting working solution was found to have a water content of 4.1 g/L (Table 1).

<Test for Activity of Working Solution>

The same procedure as shown in Example 1 was repeated to test the resulting working solution for its activity. The relative hydrogen absorption rate of this working solution was found to be 168% (Table 1).

Reference Example 3

<Hydrogenation of Distillation-Recovered Solvent>

The same procedure as shown in Example 1 was repeated, except that the reaction temperature was set to 120° C. However, the intended reaction did not proceed.

Reference Example 4

<Hydrogenation of Distillation-Recovered Solvent>

The same procedure as shown in Example 1 was repeated, except that the catalyst type was changed to SN-750 (Ni catalyst; JGC Catalysts and Chemicals Ltd., Japan) and the reaction temperature was set to 120° C. However, the intended reaction did not proceed.

Reference Example 5

<Hydrogenation of Distillation-Recovered Solvent>

The same procedure as shown in Example 1 was repeated, except that the catalyst type was changed to SN-750 (Ni catalyst; JGC Catalysts and Chemicals Ltd., Japan) and the reaction initiation temperature was set to 100° C. However, the intended reaction did not proceed, and hence the reaction temperature was elevated to 160° C. after 2 hours from the initiation of the reaction. Since hydrogen absorption was observed with elevation of the reaction temperature, the reaction was also carried out at 170° C. for 2 hours, but the content of low-boiling substances was also increased. As a result, the remaining percentage of diisobutyl ketone was found to be 14.3% by mass (Table 1).

Example 6

<Alkaline Azeotropic Treatment of Hydrogenated Solvent>

The distillation-recovered solvent was treated under the same conditions as used in Example 1, and the resulting hydrogenated solvent was subjected to alkaline azeotropic treatment as disclosed in JP Patent Publication No. 2008-87992. Namely, a distillation unit equipped with a Mellapak-filled rectifying column and a stirring unit was charged with 1.0% aqueous sodium hydroxide (100 ml), and the hydrogenated solvent obtained from the distillation-recovered solvent under the same conditions as used in Example 1 was continuously added thereto and heated to distill a mixture of the hydrogenated solvent and water. This mixture was separated in the separation chamber. The distilled water was returned again as reflux water to the distillation pot, and only the distilled and purified hydrogenated solvent was recovered. The hydrogenated solvent was supplied continuously, and its supply was stopped at the time point where the total volume reached 1000 ml. This purified hydrogenated solvent was found to have an acid value of 0 mg KOH/g (Table 1).

<Preparation of Working Solution>

Using the purified hydrogenated solvent obtained as described above, the same procedure as shown in Example 1 was repeated to prepare a working solution. This working solution was found to have a water content of 3.6 g/L (Table 1).

<Test for Activity of Working Solution>

The same procedure as shown in Example 1 was repeated to test the resulting working solution for its activity. The relative hydrogen absorption rate of this working solution was found to be 159% (Table 1).

Example 7

<Alkaline Washing of Hydrogenated Solvent>

The distillation-recovered solvent was treated under the same conditions as used in Example 1, and the resulting hydrogenated solvent was washed with an aqueous alkaline solution. The aqueous alkaline solution used for this purpose was 0.5% aqueous sodium hydroxide. The hydrogenated solvent (250 ml) and the above 0.5% aqueous sodium hydroxide (100 ml) were charged into a separatory funnel. The hydrogenated solvent and the aqueous alkaline solution were each controlled in advance to have a temperature of 30° C. This separatory funnel was mounted on a shaker (Shaker SA31, Yamato Scientific Co., Ltd., Japan) and shaken for 5 minutes at a shaking intensity of 280 times per minute. The separatory funnel was then allowed to stand for 60 minutes to separate the hydrogenated solvent and the aqueous sodium hydroxide into the upper and lower layers, respectively. From the separatory funnel, the separated upper layer, i.e., the hydrogenated solvent was recovered.

<Water Washing Treatment>

After the above alkaline washing, the recovered hydrogenated solvent was subjected to water washing treatment in the following manner. A separatory funnel was charged with the hydrogenated solvent and pure water (100 ml), followed by shaking for 5 minutes in the same manner as described above. Moreover, after shaking, the separatory funnel was allowed to stand for 60 minutes to cause separation between the hydrogenated solvent and the aqueous layer. The lower layer, i.e., the aqueous layer was removed, and fresh pure water (90 ml) was newly added, followed by repeating the same shaking operation. After shaking, the aqueous layer was removed again in the same manner. Water washing was performed again and repeated three times in total. The water temperature for this purpose was adjusted in advance to 30° C. The purified hydrogenated solvent was found to have an acid value of 31 mg KOH/g (Table 1).

<Preparation of Working Solution>

Using the hydrogenated solvent obtained as described above, the same procedure as shown in Example 1 was repeated to prepare a working solution. The resulting working solution was found to have a water content of 3.5 g/L (Table 1).

<Test for Activity of Working Solution>

The same procedure as shown in Example 1 was repeated to test the resulting working solution for its activity. The relative hydrogen absorption rate of this working solution was found to be 158% (Table 1).

Example 8

<Water Washing Treatment of Hydrogenated Solvent>

The distillation-recovered solvent was treated under the same conditions as used in Example 1, and the resulting hydrogenated solvent was washed with pure water. For water washing treatment, a countercurrent five-stage mixer-settler extractor was used, and pure water was used in an amount of 5 volumes of the hydrogenated solvent. The purified hydrogenated solvent was found to have an acid value of 64 mg KOH/g (Table 1).

<Preparation of Working Solution>

Using the hydrogenated solvent obtained as described above, the same procedure as shown in Example 1 was repeated to prepare a working solution. This working solution was found to have a water content of 3.5 g/L (Table 1).

<Test for Activity of Working Solution>

The same procedure as shown in Example 1 was repeated to test the resulting working solution for its activity. The relative hydrogen absorption rate of this working solution was found to be 155% (Table 1).

TABLE 1

| No. | Source material g | Catalyst Type | Catalyst % by mass (relative to crude solvent) | Temperature °C. | Pressure MPa | Accumulated time hr | Composition of distillation-recovered solvent (GC area ratio (%)) PSC | DIBC | DIBK | Other | Acid value Conc. [mg KOH/g] | Relative hydrogen absorption [%] | Water content g/L |
|---|---|---|---|---|---|---|---|---|---|---|---|---|---|
| Reference Example 1 | — | — | — | — | — | — | 62.4 | 11.8 | 25.4 | 0.4 | 84 | 100 | 2.4 |
| Example 1 | 900 | N203SD | 1 | 200 | 2 | 0 | 62.4 | 11.8 | 25.4 | 0.4 | 81 | 153 | 3.6 |
|  |  |  |  |  |  | 3 | 62.4 | 29.6 | 7.6 | 0.4 |  |  |  |
|  |  |  |  |  |  | 5 | 62.5 | 30.8 | 6.4 | 0.3 |  |  |  |
|  |  |  |  |  |  | 7 | 62.4 | 30.8 | 6.4 | 0.4 |  |  |  |
| Example 2 | 900 | N203SD | 0.4 | 160 | 1.6 | 0 | 62.4 | 11.8 | 25.4 | 0.4 | 82 | 151 | 3.5 |
|  |  |  |  |  |  | 10 | 62.4 | 18.2 | 19 | 0.4 |  |  |  |
|  |  |  |  |  |  | 30 | 62.2 | 23.5 | 13.7 | 0.6 |  |  |  |
|  |  |  |  |  |  | 50 | 62.3 | 28.1 | 9.1 | 0.5 |  |  |  |
|  |  |  |  |  |  | 80 | 62.2 | 30.3 | 6.9 | 0.6 |  |  |  |
| Example 3 | 900 | N203SD | 1 | 160 | 2 | 0 | 62.4 | 11.8 | 25.4 | 0.4 | 82 | 152 | 3.6 |
|  |  |  |  |  |  | 2 | 62.4 | 17.2 | 20 | 0.4 |  |  |  |
|  |  |  |  |  |  | 5 | 62.2 | 23.2 | 14 | 0.6 |  |  |  |
|  |  |  |  |  |  | 9 | 62.3 | 31.1 | 6.1 | 0.5 |  |  |  |
| Example 4 | 1800 | N203SD | 0.8 | 160 | 2 | 0 | 62.4 | 11.8 | 25.4 | 0.4 | 81 | 151 | 3.5 |
|  |  |  |  | 160 | 2 | 2 | 62.5 | 17.6 | 19.6 | 0.3 |  |  |  |
|  |  |  |  | 160 ⓡ | 2 | 5 | 62.2 | 27.1 | 10.1 | 0.6 |  |  |  |
|  |  |  |  | 200 | 2 | 8.5 | 62.3 | 30.6 | 6.6 | 0.5 |  |  |  |
| Example 5 | 900 | N203SD | 1 | 220 | 1 | 0 | 62.4 | 11.8 | 25.4 | 0.4 | 82 | 152 | 3.6 |
|  |  |  |  |  |  | 2.5 | 62.2 | 16.4 | 20.8 | 0.6 |  |  |  |
|  |  |  |  |  |  | 5 | 61.8 | 19.9 | 17.3 | 1 |  |  |  |
|  |  |  |  |  |  | 8 | 62.1 | 24.7 | 12.5 | 0.7 |  |  |  |
|  |  |  |  |  |  | 12.5 | 62.4 | 30.8 | 6.4 | 0.4 |  |  |  |

TABLE 1-continued

| | | Catalyst | | | | | Composition of distillation-recovered solvent (GC area ratio (%)) | | | | Acid value Conc. [mg KOH/g] | Relative hydrogen absorption [%] | Water content g/L |
|---|---|---|---|---|---|---|---|---|---|---|---|---|---|
| No. | Source material g | Type | % by mass (relative to crude solvent) | Temperature °C. | Pressure MPa | Accumulated time hr | PSC | DIBC | DIBK | Other | | | |
| Reference Example 2 | — | — | — | — | — | — | 60.8 | 38.1 | 1 | 0.1 | 0 | 168 | 4.1 |
| Reference Example 3 | 900 | N203SD | 1 | 120 | 2 | | — | — | — | — | — | — | — |
| Reference Example 4 | 900 | SN-750 | 1 | 120 | 2 | | — | — | — | — | — | — | — |
| Reference Example 5 | 900 | SN-750 | 1 | 100 | 2 | 0 | 62.4 | 11.8 | 25.4 | 0.4 | — | — | — |
| | | | | 100 ® | 2 | 4 | 62.2 | 13.4 | 23.8 | 0.6 | | | |
| | | | | 160 | 2 | 6 | 61.4 | 17.7 | 19.5 | 1.4 | | | |
| | | | | 160 ® | 2 | 8 | 60.5 | 22.9 | 14.3 | 2.3 | | | |
| Example 6 | 900 | N203SD | 1 | 200 | 2 | 0 | 62.4 | 11.8 | 25.4 | 0.4 | 0 | 159 | 3.6 |
| | | | | | | 3 | 62.3 | 29.4 | 7.8 | 0.5 | | | |
| | | | | | | 5 | 62.1 | 30.8 | 6.4 | 0.7 | | | |
| | | | | | | 7 | 62.2 | 30.9 | 6.3 | 0.6 | | | |
| Example 7 | 900 | N203SD | 1 | 200 | 2 | 0 | 62.4 | 11.6 | 25.4 | 0.4 | 31 | 158 | 3.5 |
| | | | | | | 3 | 62.2 | 29.2 | 7.8 | 0.8 | | | |
| | | | | | | 5 | 62.3 | 30.4 | 6.6 | 0.7 | | | |
| | | | | | | 7 | 62.2 | 30.7 | 6.3 | 0.8 | | | |
| Example 8 | 900 | N203SD | 1 | 200 | 2 | 0 | 62.4 | 11.8 | 25.4 | 0.4 | 64 | 155 | 3.5 |
| | | | | | | 3 | 62.4 | 29.4 | 7.8 | 0.4 | | | |
| | | | | | | 5 | 62.4 | 30.6 | 6.6 | 0.4 | | | |
| | | | | | | 7 | 62.3 | 30.9 | 6.3 | 0.5 | | | |

PSC: pseudocumene
DIBC:
DIBK: diisobutyl

In view of the foregoing, the efficiency of hydrogen absorption was increased in each example where the ketone form (DIBK) among the organic solvent components (i.e., the distillation-recovered solvent) in the working solution which had been used for many years was reduced to the original alcohol. Namely, the relative absorption efficiency was 100% in Reference Example 1 where the ketone form still constituted 25.4% by mass of the organic solvent components, whereas the relative absorption efficiency was improved to 150% or more in each example as a result of decreasing the ketone form in the organic solvent components to 10% by mass or less, more specifically to 6% to 7% by mass (see Table 1). This value is considered to be close to 168% obtained in Reference Example 2 where a fresh working solution was used as a sample.

Moreover, in the anthraquinone process, the efficiency of hydrogen absorption is proportional to the production efficiency of hydrogen peroxide. It was therefore confirmed that the production efficiency of hydrogen peroxide by the working solution would be improved when the remaining percentage of the ketone form in the organic solvent was adjusted to 10% by mass or less.

In addition, the following is given as a more detailed reason that the production efficiency of hydrogen peroxide was able to be improved.

In Reference Example 1 where the ketone form was contained in abundance in the organic solvent components, water was contained at a content as low as 2.4 (g/L) in the organic solvent components (i.e., the distillation-recovered solvent). In contrast, in each example where the content of the ketone form was low, it was confirmed that water was contained at a content up to 3 to 4 (g/L) which is close to the value (4.1 (g/L)) obtained in Reference Example 2 where a fresh working solution was used. Thus, a working solution with low ketone form content may contain an appropriate amount of water, so that it is possible to inhibit the generation of free water which may adversely affect the production of hydrogen peroxide. As result of inhibiting the generation of free water, the efficiency of hydrogen absorption was increased. This may be a major reason that the production efficiency of hydrogen peroxide was able to be improved.

Further, in Examples 6 to 8 where the organic solvent components were contacted with an aqueous alkaline solution or with water, the acid value was greatly decreased when compared to Reference Example 1 and the other examples (see Table 1). This result confirmed that not only the ketone form, but also other acidic impurities were able to be removed during the step of contacting the organic solvent components with an aqueous alkaline solution or with water.

Moreover, according to the present invention, ketone forms can be efficiently regenerated into the original alcohols. This is because the present invention does not require any step to selectively separate ketone forms alone from the working solution, so that organic solvent components containing, e.g., a nonpolar solvent or the like remaining therein may be separated from the working solution and these organic solvent components may be provided as such for reaction with a catalyst. Organic solvent components commonly used in the anthraquinone process can be easily separated from anthraquinone compounds, and such separation of organic solvent components is very easy when compared to the selective separation of ketone forms alone.

The invention claimed is:
1. A process for regeneration of a working solution provided for continuous use in the production of hydrogen peroxide via an anthraquinone process, the process comprising:
   distilling the working solution to separate organic solvent components containing an alcohol and the ketone form of the alcohol; and subjecting resulting organic solvent components to hydrogenation treatment in the presence of a metal catalyst to regenerate the ketone form back into the original alcohol.

2. The process according to claim 1, wherein as a result of the hydrogenation treatment of the organic solvent components in the presence of the metal catalyst, a remaining percentage of the ketone form in the organic solvent components, ketone form/organic solvent components×100, is 10% by mass or less.

3. The process according to claim 1, wherein the metal catalyst is a metal compound comprising at least one selected from the group consisting of palladium, rhodium, ruthenium, platinum, copper, and chromium.

4. The process according to claim 1, wherein the metal catalyst is a metal compound comprising copper, chromium, or a combination thereof.

5. The process according to claim 1, wherein the amount of the metal catalyst added is from 0.05% by mass to 10% by mass, relative to the mass of the organic solvent components.

6. The process according to claim 1, wherein pressure for the hydrogenation treatment is from atmospheric pressure to 10 MPa.

7. The process according to claim 1, wherein the hydrogenation treatment is carried out at a temperature of from 140° C. to 230° C.

8. The process according to claim 1, wherein the hydrogenation treatment is carried out for 0.5 hours to 100 hours.

9. The process according to claim 1, further comprising treating the organic solvent components after the hydrogenation treatment by contacting the organic solvent components with water and/or an aqueous alkaline solution.

10. A process for production of hydrogen peroxide, the process comprising:
regenerating a working solution provided for continuous use in the production of producing hydrogen peroxide via an anthraquinone process by
distilling the working solution to separate organic solvent components containing an alcohol and the ketone form of the alcohol, and
subjecting resulting organic solvent components to hydrogenation treatment in the presence of a metal catalyst to regenerate the ketone form back into the original alcohol, and
producing hydrogen peroxide via the anthraquinone process by mixing the regenerated working solution with an alkylanthraquinone, alkyltetrahydroanthraquinone or a combination thereof.

* * * * *